United States Patent
Sjölund et al.

(10) Patent No.: US 10,744,343 B2
(45) Date of Patent: Aug. 18, 2020

(54) CONVEX INVERSE PLANNING METHOD

(71) Applicant: ELEKTA LTD., Crawley (GB)

(72) Inventors: Jens Sjölund, Stockholm (SE); Håkan Nordström, Sollentuna (SE)

(73) Assignee: ELEKTA INSTRUMENT AB, Stockholm (SE)

( * ) Notice: Subject to any disclaimer, the term of this patent is extended or adjusted under 35 U.S.C. 154(b) by 401 days.

(21) Appl. No.: 15/581,283

(22) Filed: Apr. 28, 2017

(65) Prior Publication Data

US 2018/0311509 A1 Nov. 1, 2018

(51) Int. Cl.
*A61N 5/10* (2006.01)

(52) U.S. Cl.
CPC .................. *A61N 5/1031* (2013.01)

(58) Field of Classification Search
CPC ...... A61N 1/00; A61N 5/1031; A61N 5/1042; A61N 5/1067
USPC .......................................................... 378/65
See application file for complete search history.

(56) References Cited

U.S. PATENT DOCUMENTS

2008/0011945 A1* 1/2008 Maurer, Jr. ............ A61N 5/103
250/252.1

* cited by examiner

*Primary Examiner* — Courtney D Thomas
(74) *Attorney, Agent, or Firm* — Birch, Stewart, Kolasch & Birch, LLP

(57) ABSTRACT

The present invention relates to the field of radiation therapy. In particular, the present invention relates to methods for treatment planning for a radiation therapy system. The method includes setting a number of objectives reflecting clinical criteria are set for the regions of interest and generating radiation dose profiles to be delivered to these regions of interest. A convex optimization function for optimizing the delivered radiation based on the objectives is provided and dose profiles for specific treatment configurations including beam shape settings for the radiation dose profiles are calculated using the convex optimization function. Treatment plans including determining the radiation dose profiles to be delivered during treatment based on the treatment configurations are created and an optimal treatment plan that satisfies the clinical criteria is selected.

23 Claims, 10 Drawing Sheets

CONVEX INVERSE PLANNING METHOD

FIELD OF THE INVENTION

The present invention relates to the field of radiation therapy. In particular, the invention relates to methods and systems for planning and optimizing treatment sessions of a patient in radiation therapy systems.

BACKGROUND OF THE INVENTION

The development of surgical techniques has made great progress over the years. For instance, patients in need of brain surgery may instead have non-invasive surgery which drastically reduces the trauma to the patients.

One system for non-invasive surgery is the Leksell Gamma Knife® Perfexion system, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which, by itself, is insufficient to damage intervening tissue. However, tissue destruction occurs where the radiation beams from a plurality of radiation sources intersect or converge, causing the radiation to reach tissue-destruc-tive levels. The point of convergence is hereinafter referred to as the "focus point".

Treatment planning optimization inradiation therapy, including for example gamma knife radio-surgery, aims at delivering sufficiently high dose to the target volume within the patient (e.g. in treatment of tumours) at the same time as the dose delivered to adjacent normal tissue is minimized. In treatment plan optimization, at least three competing factors have to be considered: delivering a sufficiently high dose to the target volume, sparing the surrounding normal or healthy tissue and keeping the treatment time as short as possible.

The treatment plan optimization is a process including optimizing the relative isocenter locations or beam directions, the beam shape settings (e.g. collimator configuration) and the fluences. In, for example, the Leksell Gamma Knife® Perfexion system the treatment plan optimization may include optimizing number of shots being used the shot size, the shot time, and the position of the shot. The irregularity and size of a target volume greatly influence relative isocenter locations or beam directions, the beam shape settings (e.g. collimator configuration) and the fluences used to optimize the treatment.

In treatment planning, inverse treatment planning has gained more and more interest. Inverse planning generally refers to the stage in treatment planning where a deliverable treatment plan is sought, such that a number of criteria are satisfied. Inverse planning can be contrasted to forward planning, where the operator manually places, weights and shapes shots. The promises of inverse planning are shorter planning times and higher quality plans. Today, inverse planning is sometimes tightly integrated with forward planning, e.g. in the software accompanying the Gamma Knife: Leksell GammaPlan. It is based on relative isodoses and uses metrics that are well-known in radiosurgery. This facilitates the transition from forward to inverse planning, and is presumably one of the reasons for the widespread adoption of inverse planning. A downside of relative isodose-based inverse planner and the complexity of the objectives is that the resulting optimization problem is inherently difficult to solve. In realistic cases it requires a compromise between computation time and the risk of ending up in a poor local optimum. This makes it difficult to explore what trade-offs are achievable—especially in complicated cases with multiple conflicting objectives. For example, a multimetastases case where at least one metastasis is adjacent to an organ at risk. Incidentally, in such a case it might also be desirable to specify some criteria that must be met, a capability lacking in present inverse planners.

In present inverse treatment planning for Gamma Knife radiosurgery, the relative isodoses are the fundamental object of interest. This is a heuristic motivated by the dose fall-off being the steepest for a certain isodose level, which should coincide with the target boundary. Incidentally, this is true for a single shot but need not be true when the dose distribution is the sum of contributions from multiple shots. Note that utilizing steep gradients presupposes high positional accuracy. For an isocenter the decision variables are the position, collimator configuration and beam-on time. The isocenter locations are moved during the optimization and the collimator configuration is treated as a discrete element in the set of all possible collimator configurations. Organs at risk are not handled explicitly in the objective function, which can be a severe limitation. Evidently, tolerance doses for organs at risk are given in absolute dose but in the present mode of planning, absolute dose is assigned only after completing the plan. This result a in an optimization problem that is very hard in the sense that any solution method requires either extensive computations or runs the risk of returning unsatisfactory local solutions.

Hence, there is a need of more efficient methods for planning and optimizing the treatment.

SUMMARY OF THE INVENTION

An object of the present invention is to provide improved methods and systems for planning and optimizing treatment sessions of a patient in radiation therapy systems.

This and other objects are fulfilled by the present invention as defined by the independent claims. Preferred embodiments are defined by the dependent claims.

The present invention is for example used in connection with treatment planning of treatment provided by means of a radiation therapy system having a collimator body provided with several groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

The term "target volume" refers to a representation of a target of a patient to be treated during radiation therapy. The target may be a tumour to be treated with radiation therapy. Typically, the representation of the target is obtained by, for example, non-invasive image capturing using X-ray or NMR.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined period of time during which a shot is delivered to the target volume.

The present invention may also be used in connection with treatment planning of treatment provided by means of intensity modulated radiation therapy (IMRT) utilizing multi-leaf collimators (MLC). In a multi-leaf collimator radiation treatment device, electron beams are generated by an electron accelerator including an electron gun, a wave guide and a guide magnet. The electron beam impinges on a target made of high atomic number materials thereby creating ionizing radiation. The Ionizing radiation is shaped and delivered by a plurality of beamlets each having a beamlet intensity that can be modelled according to a fluence map. The fluence map is determined in the optimization.

According to an aspect of the present invention, there is provided a method for dose or treatment planning for a radiation therapy system. The radiation therapy system comprising a radiation therapy unit, wherein a spatial dose delivered can be changed by adjusting beam shape settings. The method comprises setting a number of objectives reflecting clinical criteria for regions of interest, including targets to be treated during treatment of the patient, organs at risk and/or healthy tissue and radiation dose profiles to be delivered to the target are generated. A convex optimization problem that steers the delivered radiation according to the objectives is provided and dose profiles for specific treatment configurations including beam shape settings for the radiation dose profiles are calculated using the convex optimization problem. Thereafter, a treatment plan, including determining the radiation dose profiles to be delivered during treatment based on the treatment configurations are created, wherein each radiation dose profile is modelled by a spatial dose volume distribution of radiation, the shape of the spatial distribution depending on the beam shape settings and an optimal treatment plan that satisfies the clinical criteria is selected.

According to another aspect of the present invention, there is provided a method for treatment planning for a radiation therapy system, the radiation therapy system comprising a radiation therapy unit having a fixed radiation focus point, wherein a spatial dose distribution surrounding the focus point can be changed by adjusting beam shape setting, including collimator settings, said collimator being arranged in sectors and having a plurality of collimator passage inlets directing radiation emanating from radioactive sources of a source carrier arrangement of the therapy system to the focus point. The method comprises generating isocenter positions in the target volume and setting a number of objectives reflecting clinical criteria for regions of interest, including targets to be treated during treatment of the patient, organs at risk and/or healthy tissue. Thereafter, a convex optimization problem that steers the delivered radiation according to the objectives is provided. Dose rates are calculated for specific treatment configurations including sector and collimator settings and irradiation time for the isocenters using the convex optimization problem. Then, treatment plans are created including determining shots to be delivered during treatment based on the treatment configurations, wherein each shot is modelled by a spatial dose volume distribution of radiation represented by a three-dimensional voxel representation, wherein the shape of said spatial distribution depending on the specific sector and collimator setting and irradiation time. Finally, an optimal treatment plan that satisfies the clinical criteria is selected.

According to yet another aspect of the present invention, a method is provided comprising defining a set of beam directions and modelling radiation dose profiles to be delivered to the target as a plurality of beamlets each having a beamlet intensity. A number of objectives reflecting clinical criteria for the target are set and a convex optimization problem optimizing intensity profiles of each beam to be delivered to the target based on the objectives so as to create fluence maps is provided, wherein the fluence maps define the beamlet intensities for each of the beamlets. Thereafter, treatment plans based on fluence maps and clinical criteria for the target are created and an optimal treatment plan that satisfies the clinical criteria is selected.

In embodiments of the present invention, the radiation source positions are generated as a set of continuous points in said target volume based on basis functions, wherein the points are fixed during the treatment planning.

In embodiments of the present invention, zero or one dimensional discrete elements from a basis representation including the target volume are selected. In embodiments of the present invention, the step of positioning radiation sources comprises performing a reduction process to reduce the number of radiation source positions by solving an initial instance of the convex optimization problem and subsequently excluding positions that did not yield substantial improvements to the clinical criteria in said initial instance of the problem. Shot positions may be defined to have different resolution in different dimensions. For a target of a few cc this will lead to thousands of isocenter locations with a grid resolution, $\delta$, of 1 mm. This $\delta$ is of the order of penumbra width for a 4 mm isocenter so it is not an unreasonable value to set if complicated targets are to be planned. However, thousands of positions will lead to a huge system optimization matrix, A, slowing down optimization unless tricks are used to bring down the size of A without losing a faithful description of the problem. A more refined grid method would be to allow different resolution in different regions of the target. One could imagine to increase the resolution in regions with complex geometry and/or in proximity of organs at risk. This would bring down the size of A at the expense of an extra time penalty to have an algorithm cleverly subdividing the target.

In embodiments of the present invention, the objective function of the convex optimization problem is a weighted sum, where each objective is associated with a function and a scalar weight.

In embodiments of the present invention, the objectives include delivered dose to target, delivered dose to a boundary space surrounding the target, delivered dose to regions in the three-dimensional voxel representation classified as a risk organ, and/or beam-on time penalization.

According to embodiments of the present invention, dose rates for specific treatment configurations including sector and collimator settings and irradiation time are calculated using the convex optimization problem for predetermined isocenters within the volume.

In embodiments of the present invention, a dose rate is calculated according to a dose rate kernel function, $\phi$, based on sources in a certain collimator state and sector in a certain isocenter location for a certain irradiation time.

In embodiments of the present invention, the dose is given by a function D(x) that depends linearly on x, wherein x corresponds to degrees of freedom.

In embodiments of the present invention, $D(x)=\phi*x$, and $\phi$ is a beamlet intensity or a dose rate kernel.

In embodiments of the present invention, a reduction process is performed to reduce the number of calculated dose rates, wherein a subset of dose rates that are spatially representative are selected for calculation based on an approximation of a volume representation of a delivered dose rate to the target.

According to embodiments of the present invention, the step of calculating comprises a reduction process based on truncating estimated dose rates at a predetermined level or applying a statistical model to remove estimated dose rates from the calculation.

In embodiments of the present invention, wherein the reduction process to reduce the number of calculated dose rates includes removing dose rates having an estimated value below a predetermined level from the calculation.

An optimized dose plan determined by means of the present invention, may be transferred to a radiation therapy system for use in the treatment of the patient. The dose plan determined by the invention may also or alternatively be used as input in a treatment optimization procedure where the number of shots, position of the shots and the shot sizes defined during the volume filling according to the invention serves as basis in an optimization of the number of shots, the position and the beam-on time of the respective shots and the shots sizes.

According to still another aspect of the present invention, there is provided a treatment planning computer structure in which the method according to the present invention may be implemented will be described. The treatment planning computer structure may include a calculation module configured for generating radiation dose profiles to be delivered to a target volume to be treated during a treatment of the patient, for providing a convex optimization problem that steers the delivered radiation according to the objectives, and for calculating dose profiles for specific treatment configurations including beam shape settings for the radiation dose profiles are calculated using the convex optimization problem. A treatment plan module is configured for creating treatment plans including determining the radiation dose profiles to be delivered during treatment based on the treatment configurations, wherein each radiation dose profile is modelled by a spatial dose volume distribution of radiation represented by a three-dimensional voxel representation, the shape of the spatial distribution depending on the beam shape settings. An optimizing module is configured for selecting an optimal treatment plan that satisfies the clinical criteria.

In embodiments of the present invention, the treatment plan computer structure may utilize methods according to the present invention and may be integrated into a system for delivering intensity modulated radiation treatment (IMRT) including a radiation source that generates at least one radiation beam and a structure for generating a plurality of beamlets. A multi-leaf collimator is disposed between the radiation source and the patient. The collimator is communicatively connected to the treatment planning computer structure and has a plurality of leafs for modifying the plurality of beamlets to deliver according to optimal treatment plan, i.e. a fluence map based on the beam shape settings determined, to the patient.

In further embodiments of the present invention, the treatment plan computer structure may utilize methods according to the present invention may be integrated into a radiation therapy system having a collimator body provided with several groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The collimator body is communicatively connected to the treatment planning computer structure to deliver according to optimal treatment plan to the patient.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1A:
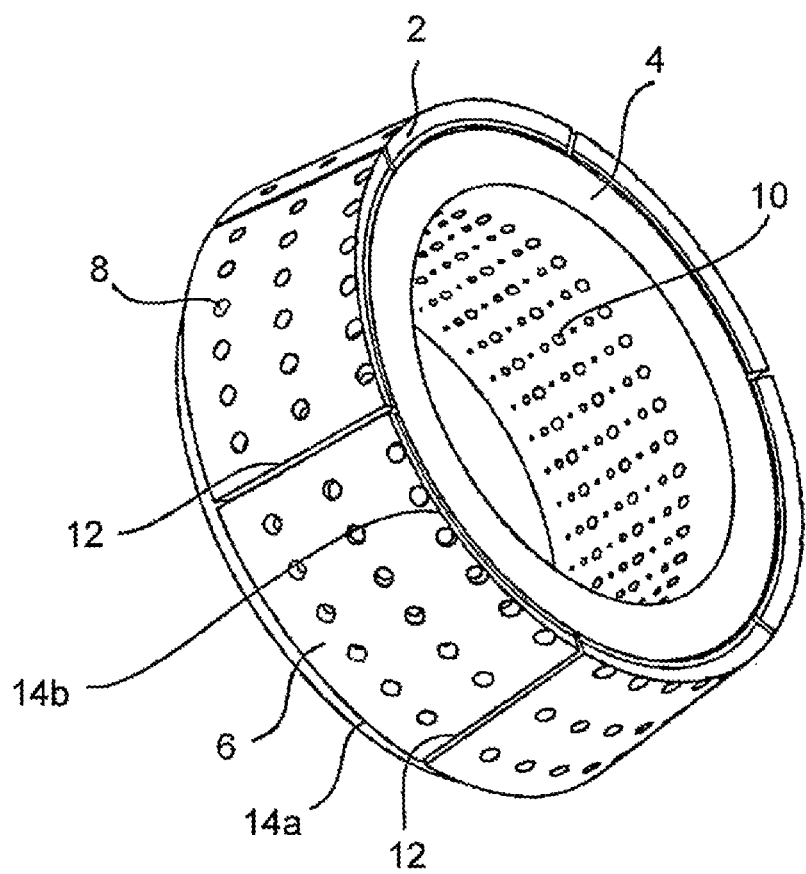
FIG. 1a is a perspective view of an assembly comprising a source carrier arrangement surrounding a collimator body in which the present invention may be used.
Figure 1B:
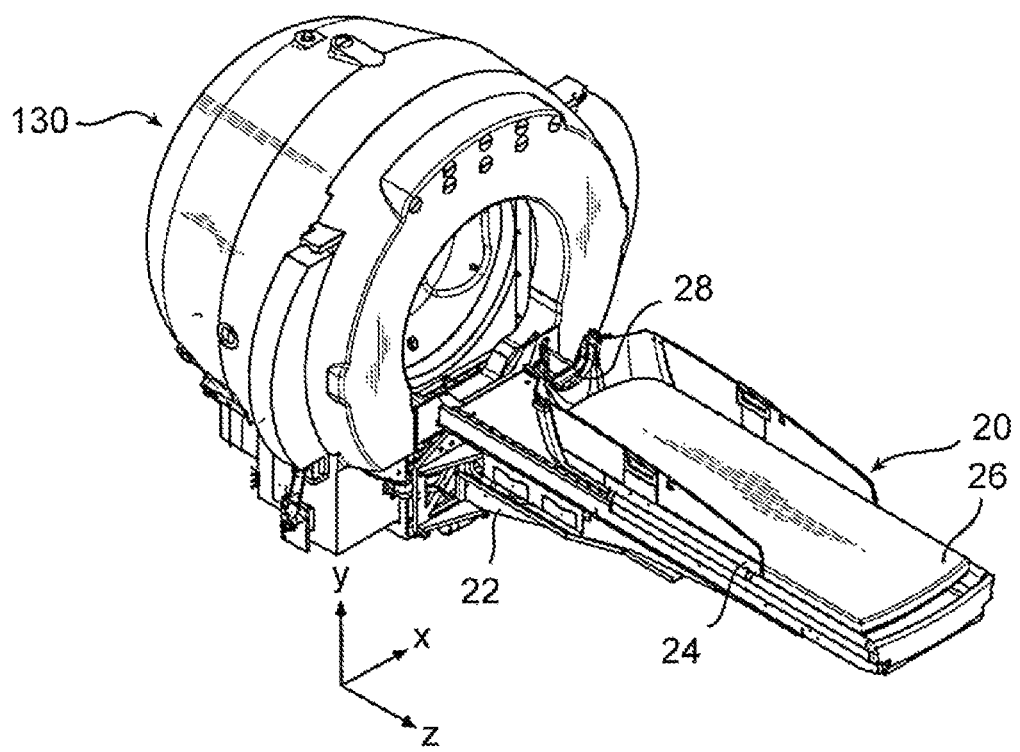
FIG. 1b shows a radiation therapy device in which the assembly of FIG. 1 may be used.

With reference first to FIGS. 1a and 1b, an exemplary radiation therapy device in which a treatment plan developed using the present invention can be used for treatment of a patient.

FIG. 1a is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1a there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

In FIG. 1b, a radiation therapy system including a radiotherapy device 130 having a source carrier arrangement as shown in FIG. 1b, and a patient positioning unit 20 is shown. In the radiation therapy unit 130, there are thus provided radioactive sources, radioactive source holders, a collimator body, and external shielding elements. The collimator body comprises a large number of collimator channels directed towards a common focus point, as shown in FIG. 1b.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit. The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Figure 2A:
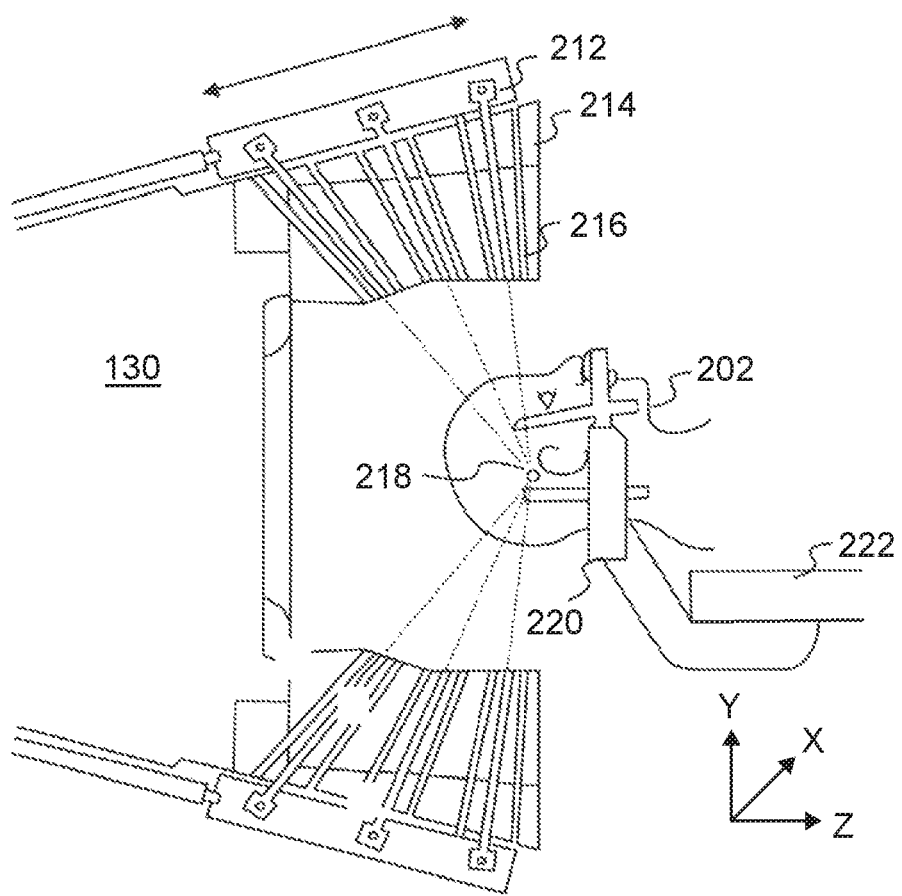
FIG. 2a shows a radiation therapy device, a Gamma Knife, in which the present invention may be used.

FIG. 2a illustrates a radiotherapy device 130, a Gamma Knife in which the present invention can be used. A patient 202 may wear a coordinate frame 220 to keep stable the patient's body part (e.g. the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 2B:
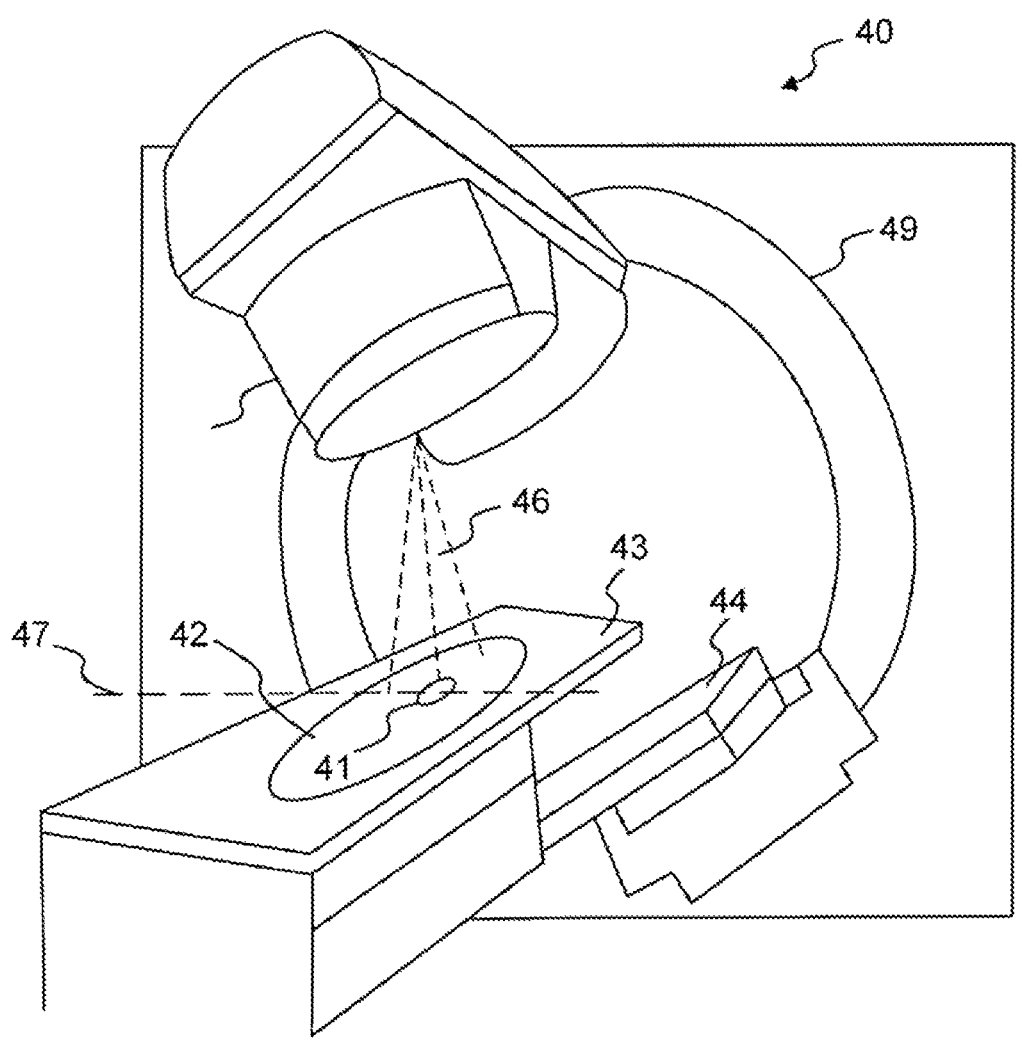
FIG. 2b shows another radiotherapy device, a linear accelerator, in which the present invention can be used.

FIG. 2b illustrates another radiotherapy device 40, a linear accelerator 10 in which the present invention can be used. Using a linear accelerator 40, a patient 42 may be positioned on a patient table 43 to receive the radiation dose determined by the treatment plan. Linear accelerator 40 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45 is usually referred to as the "isocenter". The patient table 43 may be motorized so that the patient 42 can be positioned with the tumor site at or close to the isocenter 41. The radiation head 45 may rotate about a gantry 49, to provide patient 42 with a plurality of varying dosages of radiation according to the treatment plan.

Figure 3:
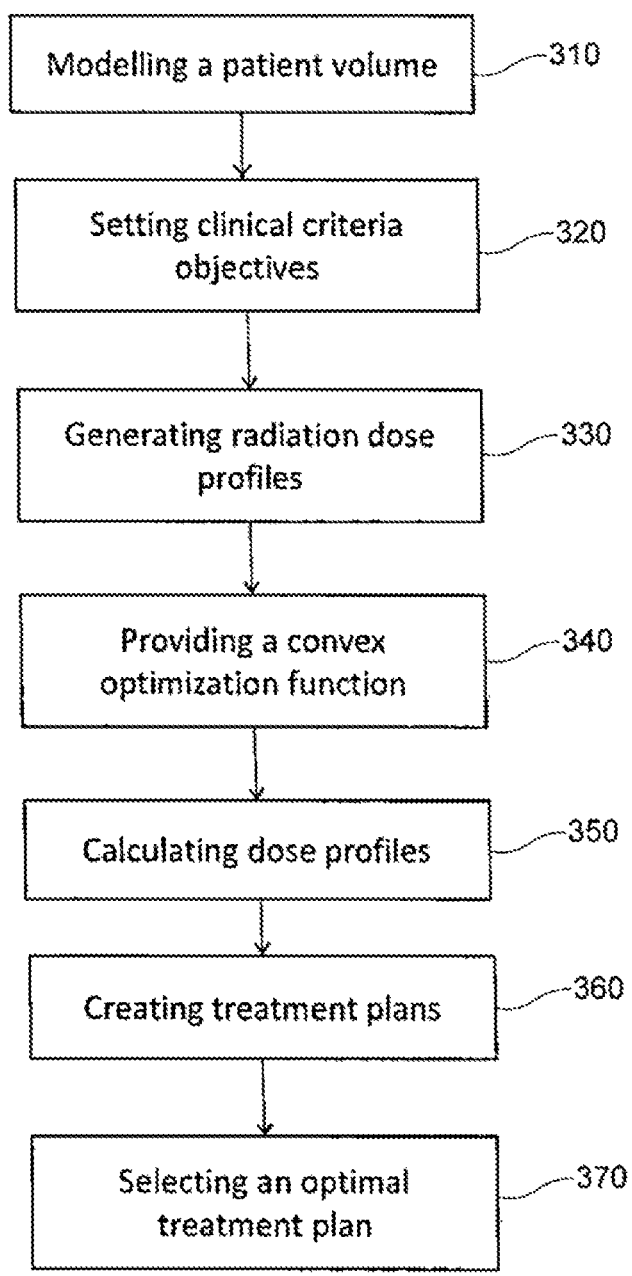
FIG. 3 is a flow diagram illustrating an embodiment of the present invention.

With reference now to FIG. 3, a general method according to the present invention will be described. The method may be used for treatment planning, for example, in intensity modulated radiation therapy (IMRT) as well as in Volumetric Arc Therapy (VMAT) utilizing multi-leaf collimators (MLC). In a multi-leaf collimator radiation treatment device, electron beams are generated by an electron accelerator including an electron gun, a wave guide and a guide magnet. The electron beam impinges on a target made of high atomic number materials thereby creating ionizing radiation. Ionizing radiation is delivered by a plurality of beamlets each having a beamlet intensity that can be modelled according to a fluence map. The fluence map is determined in the optimization. Moreover, the method may also be used in treatment planning for radiation therapy system having a collimator body provided with several groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

First, in step 310, a volume of a patient is modelled as a three-dimensional voxel representation, wherein the volume includes a target volume to be treated during a treatment of the patient in a radiation therapy unit.

Then, in step 320, a number of objectives reflecting clinical criteria are set for the target and, in step 330, radiation dose profiles to be delivered to the target are generated as well as radiation delivered to surrounding tissue.

In step 340, a convex optimization problem that steers the delivered radiation according to the objectives is provided and, in step 35, dose profiles for specific treatment configurations including beam shape settings for the radiation dose profiles are calculated using the convex optimization problem.

Thereafter, in step 360, treatment plans including determining the radiation dose profiles to be delivered during treatment based on the treatment configurations are created, wherein each radiation dose profile is modelled by a spatial dose volume distribution of radiation represented by a three-dimensional voxel representation, the shape of the spatial distribution depending on the beam shape settings. Finally, in step 37, an optimal treatment plan that satisfies the clinical criteria is selected.

Figure 4:
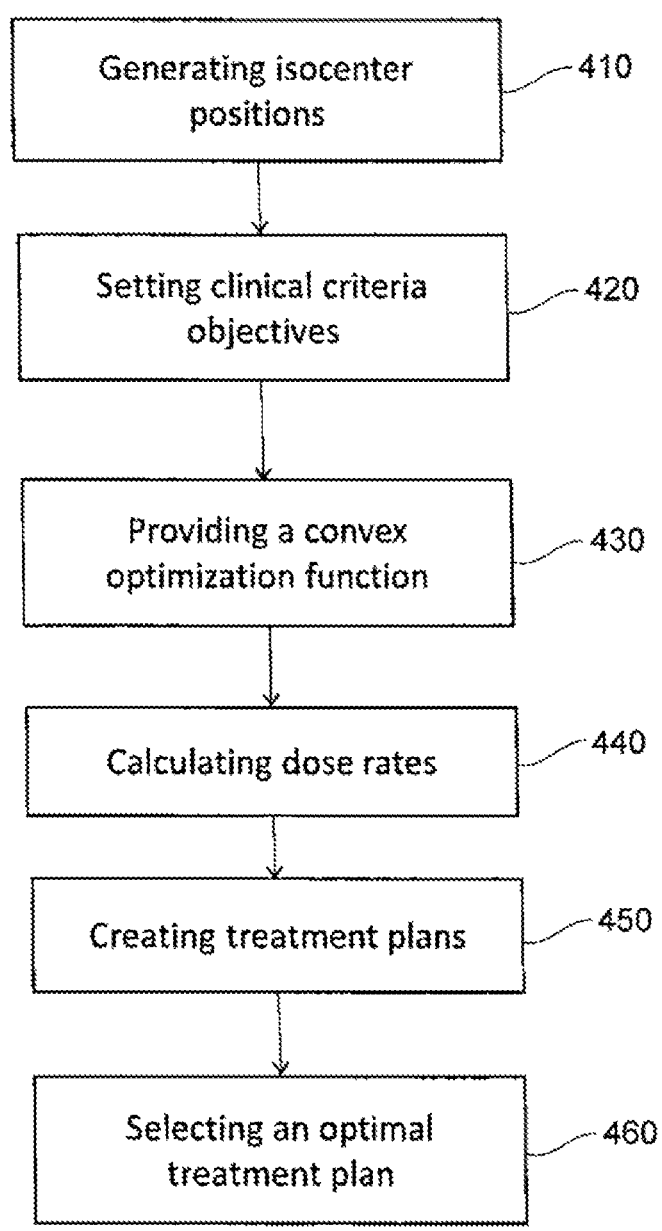
FIG. 4 is a flow diagram illustrating an embodiment of the present invention.

With reference to FIG. 4, another aspect of the present invention will be described. The method according to this aspect for treatment planning may be used in a radiation therapy system comprising a radiation therapy unit having a fixed radiation focus point, wherein a spatial dose distribution surrounding the focus point can be changed by adjusting beam shape setting, including collimator settings, said collimator being arranged in sectors and having a plurality of collimator passage inlets directing radiation emanating from radioactive sources of a source carrier arrangement of the therapy system to the focus point.

First, in step 410, isocenter positions in the target volume are generated and, in step 420, a number of objectives reflecting clinical criteria for the target are set. Thereafter, in step 430, a convex optimization problem that steers the delivered radiation according to the objectives is provided.

In step 440, dose rates are calculated for specific treatment configurations including sector and collimator settings using the convex optimization problem.

Then, in step 450, treatment plans are created including determining shots to be delivered during treatment based on the treatment configurations, wherein each shot is modelled by a spatial dose volume distribution of radiation represented by a three-dimensional voxel representation, wherein the shape of said spatial distribution depending on the specific sector and collimator setting and irradiation time. Finally, in step 460, an optimal treatment plan that satisfies the clinical criteria is selected.

Figure 5:
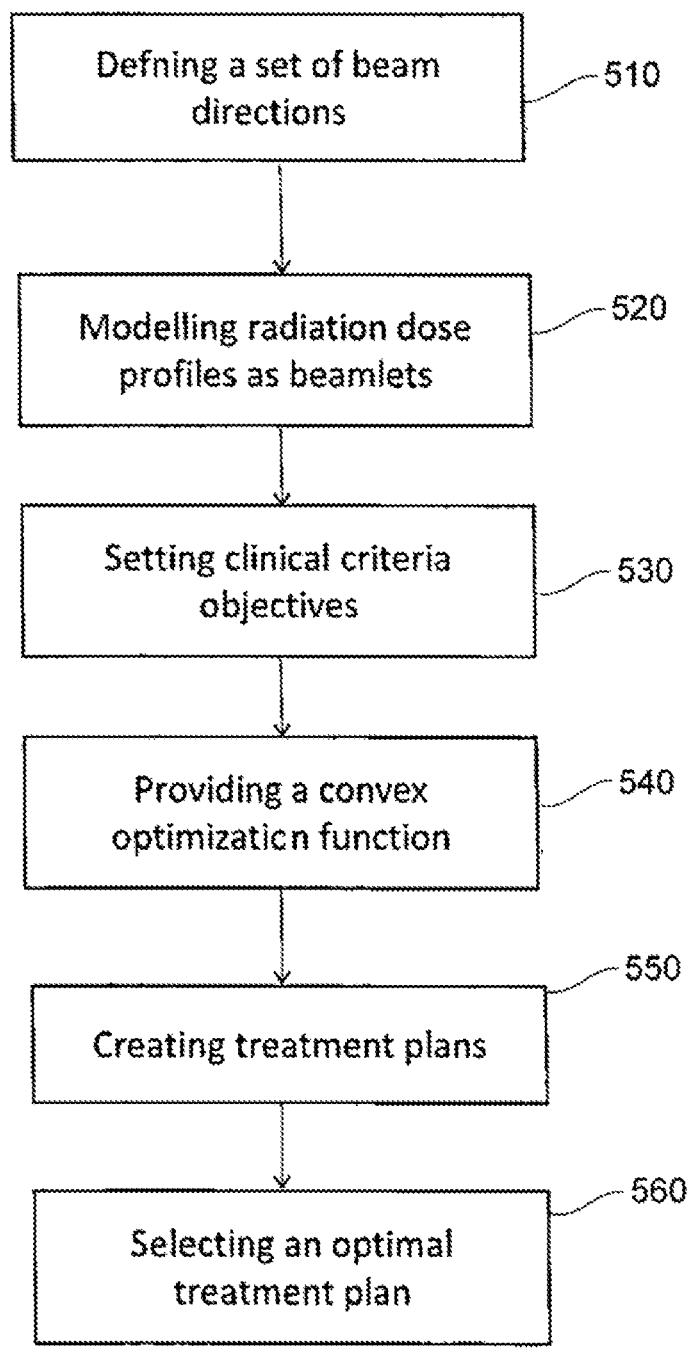
FIG. 5 is a flow diagram illustrating an embodiment of the present invention.

With reference to FIG. 5, yet another aspect of the present invention will be described. The method according to this aspect may be used in, for example, intensity modulated radiation therapy (IMRT) utilizing multi-leaf collimators (MLC) and Volumetric Arc Therapy (VMAT). In a multi-leaf collimator radiation treatment device, electron beams are generated by an electron accelerator including an electron gun, a wave guide and a guide magnet. The electron beam impinges on a target made of high atomic number materials thereby creating ionizing radiation. Ionizing radiation is delivered by a plurality of beamlets each having a beamlet intensity that can be modelled according to a fluence map. The fluence map is determined in the optimization.

First, in step 510, a set of beam directions is defined and, in step 520, radiation dose profiles to be delivered to the target are modelled as a plurality of beamlets each having a beamlet intensity.

In step 530, a number of objectives reflecting clinical criteria for the target are set and, in step 540, a convex optimization problem that steers the delivered radiation according to the objectives is provided, i.e. optimizing intensity profiles of each beam to be delivered to the target based on the objectives so as to create fluence maps, wherein the fluence maps define the beamlet intensities for each of the beamlets.

Thereafter, in step 550, treatment plans based on fluence maps and clinical criteria for the target are created and, in step 56, an optimal treatment plan that satisfies the clinical criteria is selected.

Figure 6:
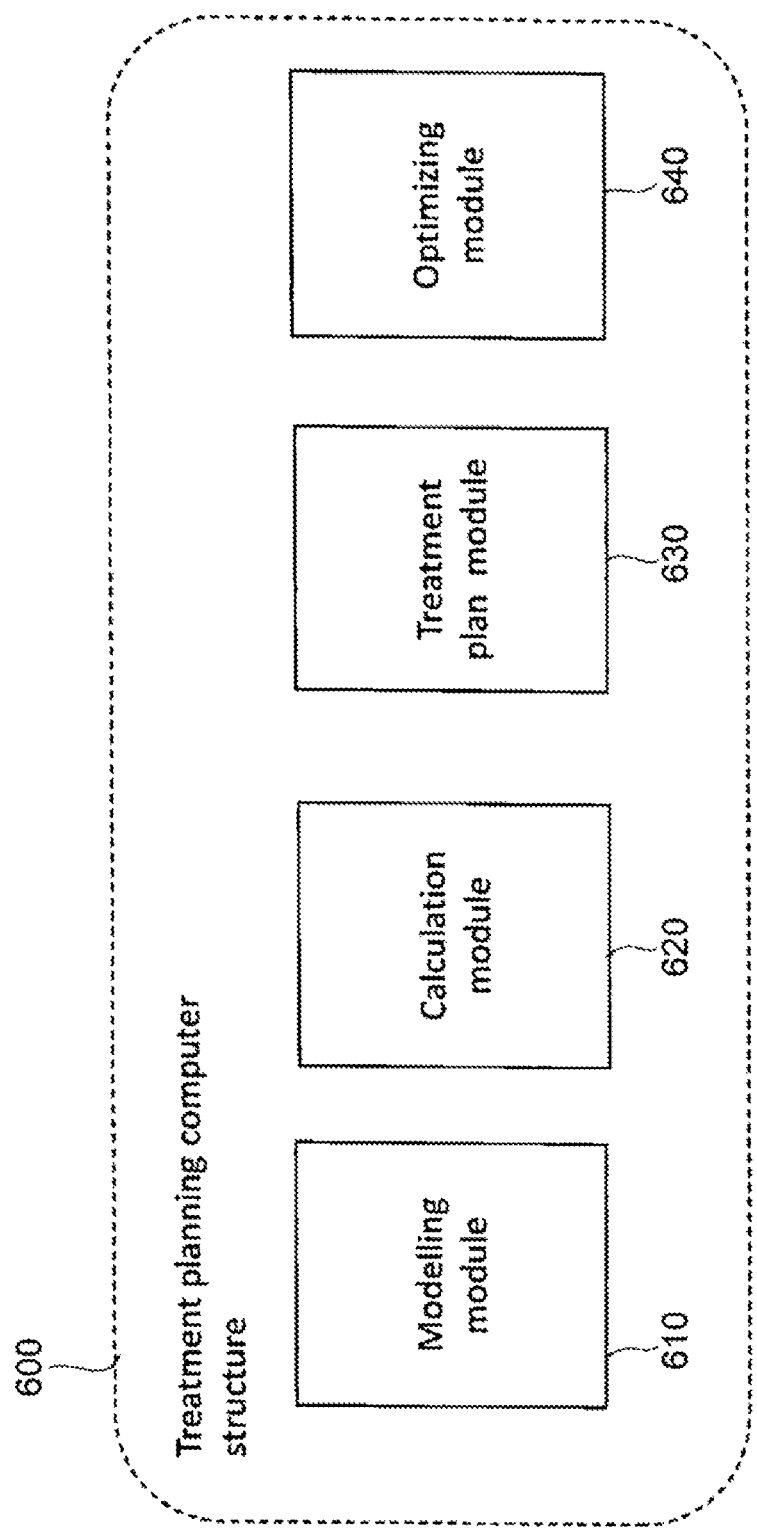
FIG. 6 shows an embodiment of a treatment planning computer structure according to the present invention.

Turning now to FIG. 6, a treatment planning computer structure in which the method according to the present invention may be implemented will be described. The treatment planning computer structure 600 may include a modelling module 610 configured for modelling a volume of a patient as a three-dimensional voxel representation or for obtaining such a three-dimensional voxel representation, wherein the volume includes a target volume to be treated during a treatment of the patient in a radiation therapy unit. Further, a calculation module 620 configured for generating radiation dose profiles to be delivered to the target, for providing a convex optimization problem that steers the delivered radiation according to the objectives, and for calculating dose profiles for specific treatment configurations including beam shape settings for the radiation dose profiles are calculated using the convex optimization problem. A treatment plan module 630 is configured for creating treatment plans including determining the radiation dose profiles to be delivered during treatment based on the treatment configurations, wherein each radiation dose profile is modelled by a spatial dose volume distribution of radiation represented by a three-dimensional voxel representation, the shape of the spatial distribution depending on the beam shape settings. An optimizing module 640 is configured for selecting an optimal treatment plan that satisfies the clinical criteria. In embodiments of the present invention, the optimization, i.e. selecting an optimal treatment plan that satisfies the clinical criteria, is performed and then the treatment plan including determining the radiation dose profiles to be delivered during treatment based on the treatment configurations is created.

In embodiments of the present invention, the treatment plan computer structure 600 may utilize a method as described in FIG. 3 or 5 and may be integrated into a system for delivering intensity modulated radiation treatment (IMRT) including a radiation source that generates at least one radiation beam and a structure for generating a plurality of beamlets. A multi-leaf collimator is disposed between the radiation source and the patient. The collimator is communicatively connected to the treatment planning computer structure and has a plurality of leafs for modifying the plurality of beamlets to deliver according to optimal treatment plan, i.e. a fluence map based on the beam shape settings determined, to the patient.

In further embodiments of the present invention, the treatment plan computer structure 600 may utilize a method as described in FIG. 3 or 4 and may be integrated into a radiation therapy system having a collimator body provided with several groups or sets of collimator passages, each set being designed to provide a radiation beam of a respective specified cross-section toward a fixed focus. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point. The collimator body is communicatively connected to the treatment planning computer structure to deliver according to optimal treatment plan to the patient.

Hence, according to embodiments of the present invention, a method for treatment or dose planning for a radiation therapy system a volume of a patient is modelled as a three-dimensional voxel representation, wherein the volume includes a target volume to be treated during a treatment of the patient in a radiation therapy unit. Often, at least a portion of the voxels is designated to belong to at least one target and/or at least one risk or critical structure. Isocenter positions in the target volume are generated and a number of objectives reflecting clinical criteria for the target are set or defined. In embodiments of the present invention, different objectives are set for different regions. For example, it might be desirable to have locally higher dose in a target regions where the oxygen delivery is impaired or lower. Moreover, it is possible to have different objectives for every voxel in a structure to thereby ensure dose painting.

Thus, a convex optimization problem that steers the delivered radiation according to the objectives is provided. The dose rates for specific treatment configurations including sector and collimator settings and irradiation time for the isocenters using the convex optimization problem are calculated. Treatment plans including shots to be delivered during treatment based on the treatment configurations are created, wherein each shot is modelled by a spatial dose volume distribution of radiation represented by a three-dimensional voxel representation, the shape of said spatial distribution depending on the specific sector and collimator setting and irradiation time. Based on this, an optimal treatment plan that satisfies the clinical criteria is selected.

As have been indicated above, the present inventions is based on convex inverse planning methods, where inverse planning refers to the stage in treatment planning where a deliverable treatment plan is sought, such that a number of criteria are satisfied. Convexity is a highly desirable property that allows optimizations problems to be solved reliably and efficiently to global optimality. In order to achieve convexity, the planning is divided into three distinct phases: relative source positioning, optimization and realization. The relative source positions (e.g. isocenters or beam directions) chosen in the first phase remain fixed throughout the rest of the planning. In the optimization phase, optimization problems are formulated where competing objectives are combined as a weighted sum. By changing the weights it is straightforward to explore the trade-offs achievable. Possible objectives include dose to target, sparing of organs at risk and beam-on time penalization The optimization problem is formulated in terms of decision variables (degrees of freedom) that are related to—but not strictly corresponding to—the machine setting used to deliver the radiation. For instance, when optimizing an IMRT plan, the fluences of all beamlets can be used as decision variables. In the realization phase, these degrees of freedom are converted into a deliverable treatment plan with the corresponding treatment modality.

Accordingly, inverse planning refers to automatically finding a treatment plan that satisfies a range of clinical criteria. This is often formulated as an optimization problem that can be solved iteratively. In each iteration a new treatment configuration is evaluated and this requires a dose calculation. The dose calculation is often the most time-consuming part of the iteration and consequently of the problem as a whole. The present invention is partly based on the insights how to efficiently and significantly speed up the dose-rate calculation while at the same time maintaining a high degree of accuracy.

Figure 7:
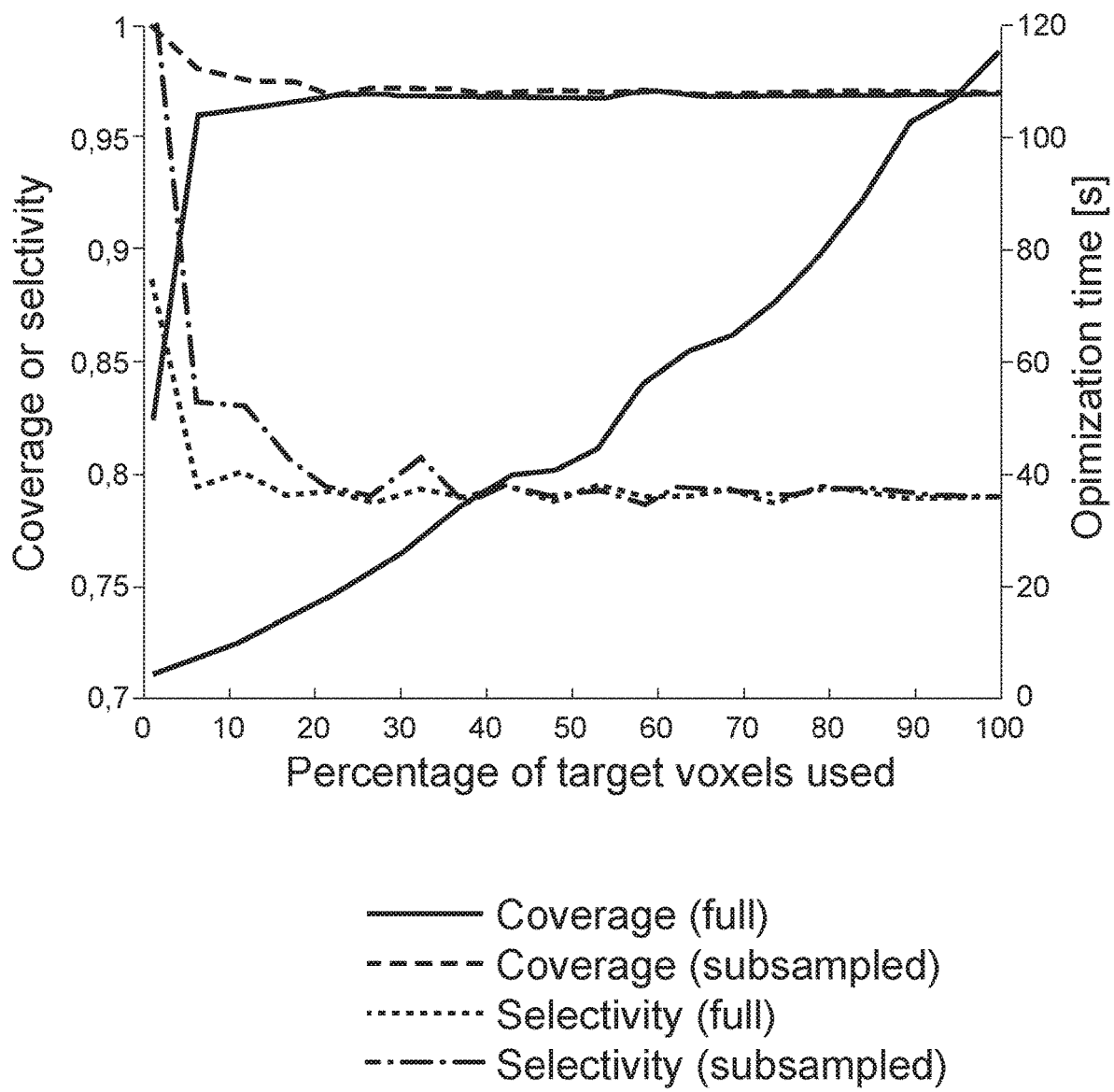
FIG. 7 is a diagram showing representative subsampling for reducing the dose-rates that needs to be calculated.

According to another aspect of the present invention for significantly speeding up the dose-rate calculation, is referred to as representative subsampling, which is analogous to polling: suppose each voxel is a voter and that you would like to know the distribution of doses in the population (e.g. voxels in target). The most accurate thing to do is to ask every voter about their dose, but this takes too much time. Instead, you may approximate the true distribution by polling a representive subset of the voters. The representative set can be chosen in a number of different ways, e.g. it can be randomly assigned or it may consist of "spokespeople" that each represent a subset of the population. As illustrated in FIG. 7, the optimization of a Gamma Knife treatment plan could be speeded-up by a factor of five with essentially no deterioration in quality by applying representative subsampling for reducing the dose-rates that needs to be calculated. This aspect of the present invention will be described in more detail below.

According to a further aspect of the present invention for significantly speeding up the dose-rate calculation, dose rates that are almost or close to zero are set to exactly zero in the model. This is beneficial since entries that are exactly zero are ignored when using sparse linear algebra for the dose calculations. As an illustrative example, with reference to FIG. 8 where a histogram of dose rates in the target of a Gamma Knife patient are shown, will be discussed. In this example, thresholding at 5% of the maximum dose rate reduces the number of nonzero element to 24% of the nominal number. The optimization time required to find a plan of equal quality was consequently reduced from 20 s to 10 s using a first solver (50%), and from 36 s to 8 s (22%) using a second solver. This aspect of the present invention will be described in more detail below.

According to the present invention, a vector of n objective functions, $$f=(f1(x), \ldots, fn(x))T$$

representing e.g. target dose, dose to an organ at risk and a penalization on the beam-on time, are determined or provided. This is referred to as a multi-criteria optimization (MCO) problem. The standard way of converting a vector valued objective function into an ordinary scalar objective function is to multiply it by a weight vector $w=(w1, \ldots, wn)T$. Each weight can be thought of as quantifying an importance of the corresponding objective. A useful concept in multi-criteria optimization is that of the Pareto surface. Simply put, the Pareto surface is the set of solutions in which you cannot improve one objective without worsening another. This means you should never be satisfied with a solution that is not on the Pareto surface (Pareto optimal) unless other considerations than explicitly expressed in the cost function is taken into account. A useful fact is that for convex multi-criteria optimization problems, every choice of weights corresponds to a Pareto optimal solution.

According to the present invention, the relative source positions within the target are fixed and are set to remain fixed throughout the optimization and realization. For example, to determine isocenter locations for a Gamma Knife treatment, existing fill algorithms can be used. Another method for identifying the relative source locations will be described below. As mentioned above, in isocenter generation in the present context it is important to find or generate fixed isocenter positions. In order to ensure convexity the isocenter locations need to be fixed during the optimization implying that finding good isocenter locations becomes even more important than for prior art optimizers. Isocenter locations in the grid are specified as:

$$r_{ijk} = \delta \times (i,j,k), i,j,k \in Z$$

With a grid resolution, $\delta$, of 1 mm and a target of a few cc this will lead to thousands of isocenter locations. This $\delta$ is of the order of penumbra width for a 4 mm isocenter so it is not an unreasonable value to set if complicated targets are to be planned. Note that a trivial extension is to have different resolutions in different dimensions, e.g. allow different resolution in different regions of the target or to increase the resolution in regions with complex geometry and/or in proximity of organs at risk or to have non-uniformly spaced isocenter locations. Thousands of grid points will lead to a huge system optimization matrix, A. For a reasonable clinical plan this implies that size(A) could be $10^{3-4} \times 10^{4-5}$ leading to memory issues and very long optimization times.

Using the techniques referred to as represenative subsampling, the size of A can be significantly reduced while still giving a faithful description of the problem.

Call $A_r$ the reduced optimization matrix. The size of $A_r$ is of the order 10-100 times less than size(A). The optimization problem to be solved is then a linear programming problem:

| | |
|---|---|
| Minimize | $c^T x$ |
| Subject to | $Bx \leq b$ |
| | $x \geq 0$ |

Where c and B are constituents in $A_r$ and x is a vector of the irradiation times for all the sectors. The above formulation promotes sparse x, i.e. only a few elements in x are non-zero which means that only a few of the originally chosen grid points are chosen as isocenter locations for the subsequent optimization. This has been verified in several numerical experiments: in one case 239 original grid points lead to a solution with 25 isocenter locations. This required a modest computation time of about 10 s. The plan resulting from a subsequent optimization with these isocenter locations had a distinctively higher quality than an optimized plan based on the fill algorithm in Leksell Gamma Plan with a similar number of isocenters for the same total Beam on time.

In another example, the relative source positioning may consist of choosing a set of beam orientations from which the radiation will be delivered. For IMRT, both co-planar and non-coplanar beam orientations are employed in clinical practice. Regardless, the set of feasible beam orientations may be represented as a (possibly large) number of discrete beam orientations that could be chosen in a number of ways. One is to choose a coordinate system and to discretize it uniformly, e.g. in the planar case one could use 72 beam angles equally spaced on the circle (5 degrees apart). Another possibility would be to sample beam orientations according to a predefined probability distribution. A third possibility would be to use an optimization procedure to generate beam orientations.

In order to obtain a convex optimization problem it is not enough that the objective functions are convex in dose—it must also hold that dose is convex with respect to its degrees of freedom (DOF). In the present inverse planner the DOFs are position, weight and collimator configuration for each isocenter, i.e. 5 DOFs for each isocenter for a total of 5Nisoc. Position and weight contribute 4 real-valued DOFs per isocenter. The collimator state is discrete, taking one out of 65535 possible states at each isocenter. As is apparent from the collimators' dose profiles the dose is not convex for any reasonably large shift in position. Thus in order to be convex in dose, positions have to be fixed during the optimization. A way to compensate for the resulting loss of DOFs while retaining a convex problem is to allow the time (or weight) of each sector (eight of them) and collimator aperture size (three of them) to vary independently for every isocenter. In total this gives us 24Nisoc real-valued, non-negative, DOFs. In this case the dose at an arbitrary point x in the head is calculated as:

$$D(x) = \sum_{k=1}^{N_{isoc}} \sum_{l=1}^{8} \sum_{m=1}^{3} \phi(x, \xi k) \times t_{klm} \equiv \phi\, TT,$$

where $\phi lm(x, \xi k)$ is the dose rate kernel from sources in collimator state m (m=1 ... 3) and sector l(l=1 ... 8) at isocenter location $\xi k$ (k=1 ... $N_{isoc}$) and $t_{klm}$ is the corresponding irradiation time.

The dose calculation can be conveniently expressed as a matrix multiplication making the convexity of the dose calculation apparent. The dose rate kernel matrix can be calculated once the isocenter positions have been chosen. Since this only needs to be done once, a more accurate algorithm like e.g. convolution can be used without a too large simulation overhead.

The size of $\phi$ is $24 N_{isoc} \times N_{dose\ points}$ and can thus be quite large, potentially slowing down the optimization.

As discussed above, according to the present invention, an objective function used and shown to be very efficient is a beam-on time penalization:

$$f_{iBOT}(t) = \sum_{i=1}^{N_{iso}} \max_{s} \sum_{c \in \{4,8,16\}} t_{isc*}$$

Here, the indices i, and c refer to the isocenter, sector and collimator aperture, respectively. We refer to this function as iBOT (idealized Beam-On Time) since it yields the beam-on time in an idealized case where collimators and isocenters can be changed instantly. Consequently, we expect it to work best in cases where beam-on times are substantially longer than the times in between shots.

Turning now to FIG. 7, a method called representative subsampling will be described. When it comes to optimizing radiotherapy plans, the dose more or less always enters in some part of the problem. Examples include: no voxel in the cochlea should receive more than 10 Gy; 95% of the target voxels should receive more than 13 Gy. These criteria could enter in the objective function of the optimization or in the constraints. To evaluate how such criteria are met requires the evaluation of the dose $D(x, \theta)$ at position x given settings $\theta$. The settings in question can be e.g. shot positions, beam-on times and sector configurations.

In so called fluence map optimization—which for the Gamma Knife corresponds to optimization with fixed shot position—the dose calculation reduces to a matrix multiplication $D(r, x) = \Phi x$, where $\Phi \in R^{m \times n}$ is a matrix mapping then settings into doses in them voxels.

Generally speaking, most of the criteria involving dose to a structure SI can be phrased as a volume integral of a function $\in(x, D)$ $$f(\theta) = \int \int_\Omega \int \epsilon(x, D(x, \theta))dx. \quad (1)$$

A simple example of such a function is the quadratic deviation from an ideal dose $\hat{D}$, $$\epsilon(x,D)=\|D(x,\theta)\hat{D}\|^2 \quad (2)$$

Another is $$\epsilon(x, D) = \begin{cases} \dfrac{1}{vol(\Omega)} & \text{if } D \geq \hat{D} \\ 0 & \text{if } D < \hat{D} \end{cases} \quad (3)$$

for which the resulting $f(\theta)$ is the coverage.

Normally, equation (1) is evaluated by discretizing the integrand on a fine grid (sometimes referred to as the dose grid) and replacing the integral with a summation. Our invention, representative subsampling, consist of replacing the integral in (1) with a more clever estimate.

Numerical integration methods can generally be described as combining evaluations of the integrand to get an approximation to the integral. The integrand is evaluated at a finite set of points called integration points and a weighted sum of these values is used to approximate the integral. One example is to randomly select a (possibly small) number of positions and replace the integral by a summation. This particular type of estimate is referred to as Monte Carlo integration. Other conceivable alternatives include:

Coarse grid with equally spaced points but smooth interpolation (e.g. Newton-Cotes formulas)
Coarse grid with adaptively chosen points (e.g. Gaussian quadrature)
A multiresolution approach (similar to multigrid methods) that employs a hierarchy of discretizations and moves between coarse and fine grids
Starting with a coarse grid in the first iterations and successively refining it as the optimization progresses.

Figure 8:
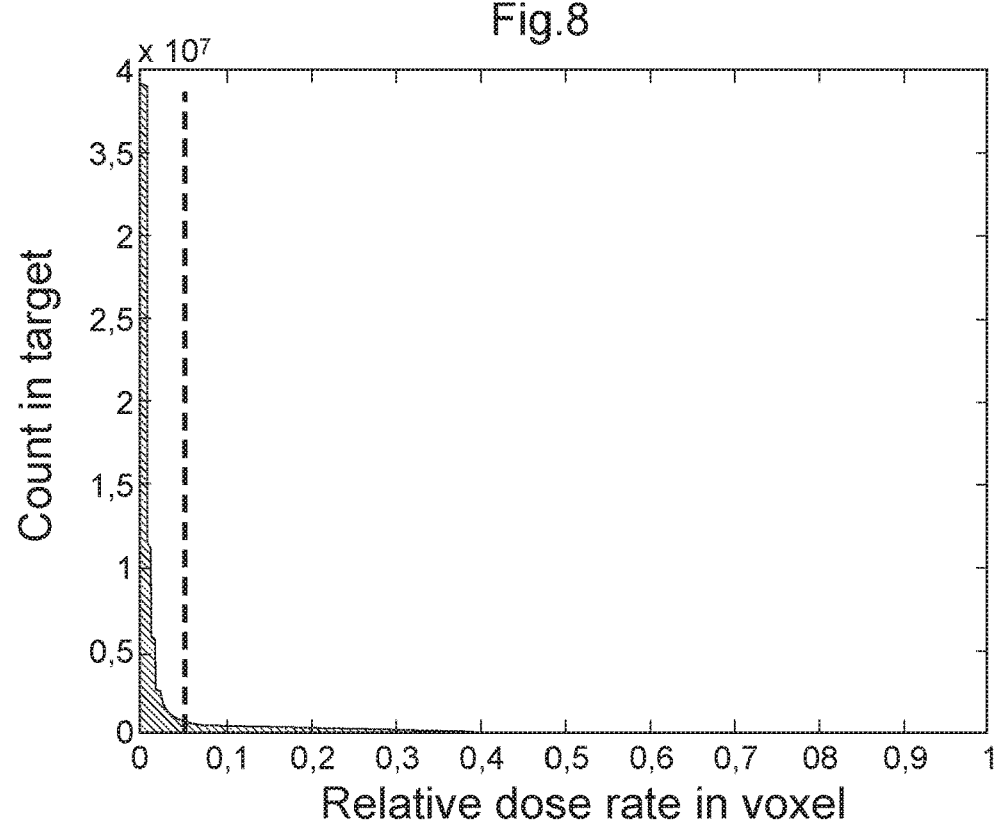
FIG. 8 is a diagram showing histogram of dose rates in the target of a Gamma Knife patient.

Referring now to FIG. 8, a method called sparse dose calculation will be described. A characteristic dose kernel for the Gamma Knife has a high dose rate near the isocenter that initially falls of quickly but has a very long tail of small dose rates, as shown in FIG. 8. The simplest realization of sparse dose calculations is to truncate the dose kernel at a suitably low value. Alternative, statistical methods such as importance sampling can be used.

A side effect of truncation is that doses are systematically underestimated (biased). This can easily be compensated by decreasing the weight of the objective function part corresponding to the target and increasing the weight of the objective function part corresponding to surrounding healthy tissue. However, if hard dose constraints are imposed, e.g. that the maximum dose in the optic nerve can't exceed 10 Gy, then this approach is not suitable for that region. Incidentally, this illustrates the possibility of having different thresholds for different regions.

Below, in table 1, treatment quality parameters and optimization time from two different Gamma Knife cases are shown. In both cases, the nominal treatment plan is compared to truncating values below 5% of the maximum dose rate and reweighting.

TABLE 1

| | GFRAME41 (nominal) | GFRAME41 (sparse) | GFRAME42 (nominal) | GFRAME42 (sparse) |
|---|---|---|---|---|
| Coverage | 0.965 | 0.96 | 0.965 | 0.96 |
| Selectivity | 0.86 | 0.86 | 0.81 | 0.80 |
| Beam-on time | 84 | 84 | 117 | 121 |
| Optimization time (s) | 36 | 8 | 45 | 18 |

A more refined alternative to avoid the bias resulting from truncation is to use a technique such as importance samling. The idea behind importance sampling is that certain values in a simulation have more impact on the parameter being estimated than others. If these "important" values are emphasized by sampling more frequently, then the estimator variance can be reduced. Hence, the basic methodology in importance sampling is to choose a distribution which "encourages" the important values. This use of "biased" distributions will result in a biased estimator if it is applied directly in the simulation. However, the simulation outputs are weighted to correct for the use of the biased distribution, and this ensures that the new importance sampling estimator is unbiased.

For example, let $f(\theta)$ denote the probability distribution for elements $\phi$ in $\Phi$. If we want to estimate the expected value of $\phi$ with as few samples as possibly, then it can be shown that the variance of the estimate is minimized by the sampling distribution $$g(\phi) = \frac{|\phi|f(\phi)}{\int |\phi|f(\phi)d\phi}$$

Figure 9:
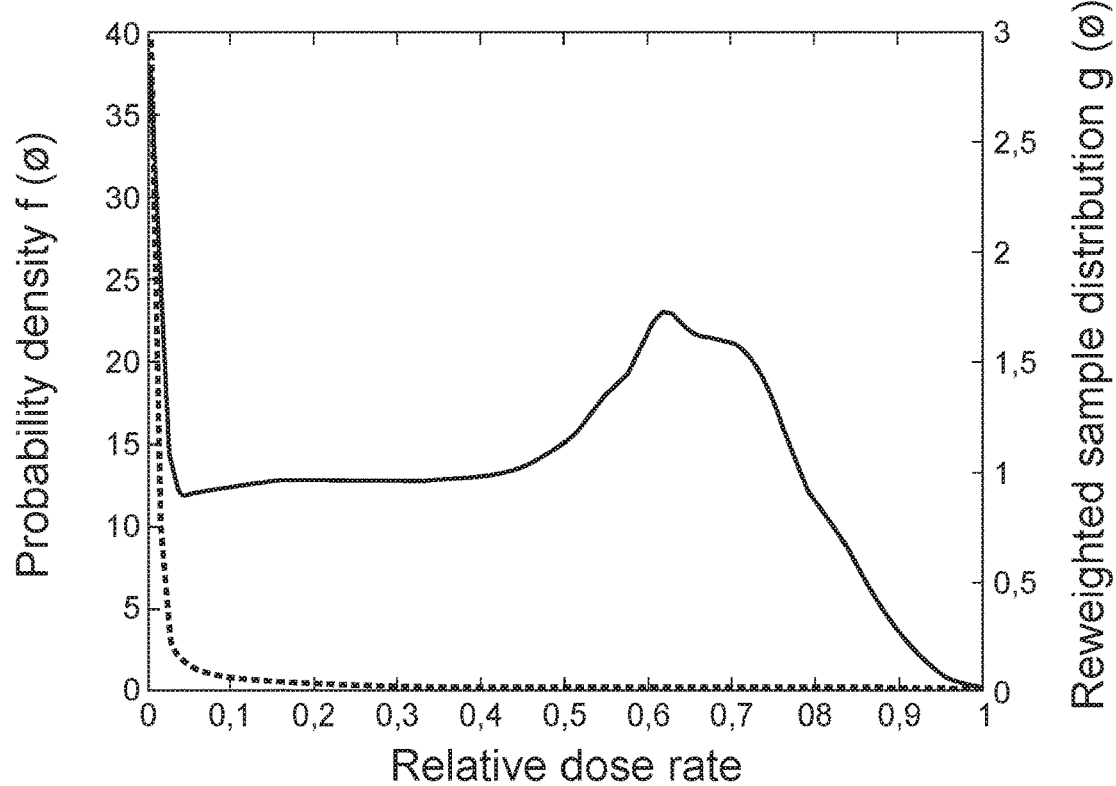
FIG. 9 is a diagram showing a dose kernel for the Gamma Knife.

To get an unbiased result, each samples needs to be weighted by the likelihood ratio $f(\phi)/g(\phi)$. FIG. 9 illustrates what $f(\phi)$ and $g(\phi)$ look like for a dose kernel used in a Gamma Knife plan.

Results

Now results using the present invention to create treatment plans for five Leksell GammaPlan (LGP) reference cases will be discussed. Various combinations of objective functions and constraints were evaluated. A general conclusion is that linear and quadratic dose penalties give comparable results, but that a linear formulation is on the order of three to five times faster. A characteristic of optimizing with a linear penalty is that doses are often pushed to be exactly at the threshold dose $\hat{D}$, a whereas a quadratic penalization gives a more spread-out dose histogram. It was found useful to employ hard constraints for serial organs at risk OAR (where the maximum dose is of most concern) and when requiring 100% coverage (possibly metastases). To promote selectivity and gradient index, a ring encompassing the target as a region of interest was defined where we penalized doses exceeding half of the prescription dose. In the terminology of regular radiotherapy, it could be compared to CTV-GTV or PTV-CTV, although we found that the exact definition was of minor importance.

Below, each of the five LGP reference cases will be presented. For each case, two plans optimized with the candidate inverse planner are presented: one emphasizing short beam-on time and one emphasizing plan quality.

The reference cases were: Large left-sided Cavernous Sinus Meningioma, Irregular left sided Cavernous Sinus Meningioma close to optic nerve, Left-sided Acoustic Neuroma of typical shape, Arteriovenous malformation, and Metastases case with one cluster of metastases and one metastasis adjacent to the brainstem. In the first example, the following was used: Dose prescription: 15Gy PTV coverage: >=95% Max 1 mm3 (Chiasm): <=8Gy Max 1 mm3 (Lt Optic Tract): <=8Gy

TABLE 2

|  | Clinical Plan | Promoting short BOT | Promoting plan quality |
|---|---|---|---|
| Coverage | 0.95 | 0.96 | 0.97 |
| Selectivity | 0.88 | 0.86 | 0.86 |
| GI | 2.73 | 2.55 | 2.40 |
| BOT @ 2.669 Gy/min | 99.8 | 83.1 | 121.2 |
| Max 1 mm$^3$ (Lt Optic nerve) | 8.95 | 8.35 | 7.65 |
| Max 1 mm$^3$ (Lt Optic tract) | 7.3 | 7.6 | 6.75 |
| Max 1 mm$^3$ (Chiasm) | 7.3 | 7.5 | 6.55 |
| V10 (cm$^3$) | 31.88 | 32.25 | 31.6 |
| Planning Isodose(%) | 46 | 60 | 58 |
| Opt time (s) |  | 188 | 184 |

TABLE 3

|  | ROI | FRACTION EVALUATED | FUNCTION | PARAMETER | WEIGHT |
|---|---|---|---|---|---|
| PROMOTING SHORT BOT | Target | 0.13 | Left Linear Auxiliary | $\hat{D} = 15.2$ | 0.54 |
|  | Outer ring | 0.04 | Right Linear Auxiliary | $\hat{D} = 7.3$ | 0.03 |
|  | Lt optic nerve | 1 | Hard constraint | $D \leq 7.8$ | — |
|  | Lt optic tract | 1 | Hard constraint | $D \leq 7.8$ | — |
|  | Chiasm | 1 | Hard constraint | $D \leq 7.8$ | — |
|  | BOT | 1 | iBOT | $\hat{t} = 15$ | 0.43 |
|  | All times | 1 | Bound | $D \geq 0$ | — |
| PROMOTING PLAN QUALITY | Target | 0.13 | Left Linear Auxiliary | $\hat{D} = 15.5$ | 0.65 |
|  | Outer ring | 0.04 | Right Linear Auxiliary | $\hat{D} = 7.0$ | 0.03 |
|  | Lt optic nerve | 1 | Hard constraint | $D \leq 7.0$ | — |
|  | Lt optic tract | 1 | Hard constraint | $D \leq 7.0$ | — |
|  | Chiasm | 1 | Hard constraint | $D \leq 7.0$ | — |
|  | BOT | 1 | iBOT | $\hat{t} = 15$ | 0.32 |
|  | All times | 1 | Bound | $D \geq 0$ | — |

Second Dose prescription: 15 Gy PTV coverage: >=95%
Max 1 mm3 (Lt Optic nerve): <=8Gy

TABLE 4

|  | Clinical Plan | Promoting short BOT | Promoting plan quality |
|---|---|---|---|
| Coverage | 0.95 | 0.97 | 0.95 |
| Selectivity | 0.78 | 0.74 | 0.82 |
| GI | 2.99 | 2.98 | 2.93 |
| BOT @ 2.698 Gy/min | 94 | 76 | 117 |
| Max 1 mm$^3$ (Lt Optic nerve) | 9.9 | 8.3 | 8.3 |
| Planning Isodose(%) | 50 | 62 | 56 |
| Optimization time(s) |  | 40 | 53 |

Third Dose prescription: 13Gy PTV coverage: >=95%
Max 1 mm3 (cochlea): <=8Gy

TABLE 6

|  | Clinical Plan | Promoting short BOT | Promoting plan quality |
|---|---|---|---|
| Coverage | 0.97 | 0.98 | 0.96 |
| Selectivity | 0.90 | 0.86 | 0.93 |
| GI | 2.78 | 3.19 | 2.68 |
| BOT @ 3.306 Gy/min | 30.4 | 17.5 | 44.1 |
| Max 1 mm$^3$ (Cochlea) | 9.9 | 8.4 | 8.3 |
| Planning Isodose (%) | 49 | 59 | 42 |
| Optimization time (s) |  | 79 | 79 |

TABLE 5

|  | ROI | FRACTION EVALUATED | FUNCTION | PARAMETER | WEIGHT |
|---|---|---|---|---|---|
| PROMOTING SHORT BOT | Target | 0.04 | Left Quadratic Auxiliary | $\hat{D} = 16$ | 0.95 |
|  | Outer ring | 0.01 | Right Linear Auxiliary | $\hat{D} = 6.5$ | 0.005 |
|  | Lt optic nerve | 1 | Hard constraint | $D \leq 7.8$ | — |
|  | BOT | 1 | iBOT | $\hat{t} = 15$ | 0.05 |
|  | All times | 1 | Bound | $D \geq 0$ | — |
| PROMOTING PLAN QUALITY | Target | 0.04 | Left Linear Auxiliary | $\hat{D} = 15.2$ | 0.77 |
|  | Outer ring | 0.01 | Right Linear Auxiliary | $\hat{D} = 7.3$ | 0.08 |
|  | Lt optic nerve | 1 | Hard constraint | $D \leq 7.8$ | — |
|  | BOT | 1 | iBOT | $\hat{t} = 15$ | 0.15 |
|  | All times | 1 | Bound | $D \geq 0$ | — |

TABLE 7

| ROI | FRACTION EVALUATED | FUNCTION | PARAMETER | WEIGHT |
|---|---|---|---|---|
| PROMOTING SHORT BOT | Target | 1 | Left Linear Auxiliary | $\hat{D} = 13.2$ | 0.78 |
| | Outer ring | 0.11 | Right Linear Auxiliary | $\hat{D} = 6.3$ | 0.02 |
| | Cochlea | 1 | Hard constraint | $D \leq 8$ | — |
| | BOT | 1 | iBOT | $\hat{t} = 13$ | 0.20 |
| | All times | 1 | Bound | $D \geq 0$ | — |
| PROMOTING PLAN QUALITY | Target | 1 | Left Linear Auxiliary | $\hat{D} = 13.2$ | 0.83 |
| | Outer ring | 0.11 | Right Linear Auxiliary | $\hat{D} = 6.3$ | 0.08 |
| | Cochlea | 1 | Hard constraint | $D \leq 8$ | — |
| | BOT | 1 | iBOT | $\hat{t} = 13$ | 0.08 |
| | All times | 1 | Bound | $D \geq 0$ | — |

Fourth Dose prescription: 25Gy PTV coverage: >95%

TABLE 8

| | Clinical Plan | Promoting short BOT | Promoting plan quality |
|---|---|---|---|
| Coverage | 0.97 | 0.96 | 0.98 |
| Selectivity | 0.89 | 0.87 | 0.91 |
| GI | 2.64 | 3.03 | 2.77 |
| BOT @ 3.481 Gy/min | 29.7 | 16.4 | 31.7 |
| V10 (cm³) | 14.98 | 17.3 | 15.51 |
| Planning Isodose(%) | 50 | 65 | 61 |
| Optimization time (s) | | 104 | 32 |

TABLE 9

| ROI | FRACTION EVALUATED | FUNCTION | PARAMETER | WEIGHT |
|---|---|---|---|---|
| PROMOTING SHORT BOT | Target | 0.34 | Left Linear Auxiliary | $\hat{D} = 25.2$ | 0.16 |
| | Outer ring | 0.04 | Right Linear Auxiliary | $\hat{D} = 12.3$ | 0.02 |
| | BOT | 1 | iBOT | $\hat{t} = 25$ | 0.82 |
| | All times | 1 | Bound | $D \geq 0$ | — |
| PROMOTING PLAN QUALITY | Target | 0.17 | Left Linear Auxiliary | $\hat{D} = 25.2$ | 0.48 |
| | Outer ring | 0.02 | Right Linear Auxiliary | $\hat{D} = 12.3$ | 0.05 |
| | BOT | 1 | iBOT | $\hat{t} = 25$ | 0.48 |
| | All times | 1 | Bound | $D \geq 0$ | — |

Fifth Dose prescription: 15 Gy to metastasis adjacent to brainstem, and 20 Gy to the five others PTV coverage: >=98%

TABLE 10

| | Target | Clinical Plan | Promoting short BOT (39 isocenters from start) | Promoting plan quality (69 isocenters from start) |
|---|---|---|---|---|
| Coverage | A | 0.99 | 0.98 | 0.99 |
| | B | 0.98 | 0.99 | 1 |
| | C | 0.98 | 1 | 0.99 |
| | D | 1 | 1 | 0.99 |
| | E | 1 | 0.99 | 1 |
| | F | 0.99 | 1 | 1 |
| Selectivity | A | 0.79 | 0.68 | 0.71 |
| | B | 0.74 | 0.64 | 0.65 |
| | C | 0.77 | 0.6 | 0.72 |
| | D | 0.62 | 0.36 | 0.65 |
| | E | 0.09 | 0.07 | 0.17 |
| | F | 0.6 | 0.54 | 0.48 |
| GI | A | 2.57 | 3.36 | 2.81 |
| | B | — | 4.07 | 3.14 |
| | C | 2.79 | 4.8 | 3.63 |
| | D | 3.23 | 3.1 | 4.17 |
| | E | — | — | 2.55 |
| | F | 3.34 | 4.1 | 3.56 |
| Planning isodose | A | 51 | 58 | 52 |
| | B | 50 | 67 | 56 |
| | C | 60 | 80 | 59 |
| | D | 56 | 73 | 64 |
| | E | 57 | 92 | 81 |
| | F | 82 | 68 | 70 |
| BOT @1,524 Gy/min | | 154.7 | 103 | 119.5 |
| V10 (cm³) | | 18.18 | 30.33 | 23.37 |
| Optimization time (s) | | | 73 | 233 |

TABLE 11

| | ROI | FRACTION EVALUATED | FUNCTION | PARAMETER | WEIGHT |
|---|---|---|---|---|---|
| PROMOTING SHORT BOT | Target A | 0.12 | Hard constraint | $D \geq 14.5$ | — |
| | Target B | 0.10 | Hard constraint | $D \geq 19.5$ | — |
| | Target C | 0.78 | Hard constraint | $D \geq 19.75$ | — |
| | Target D | 0.99 | Hard constraint | $D \geq 19.75$ | — |
| | Target E | 1 | Hard constraint | $D \geq 19.5$ | — |
| | Target F | 1 | Hard constraint | $D \geq 19.6$ | — |
| | Outer ring A | 0.001 | Right Linear Auxiliary | $\hat{D} = 6.75$ | 0.0016 |
| | Outer ring B | 0.001 | Right Linear Auxiliary | $\hat{D} = 9.5$ | 0.0033 |
| | Outer ring C | 0.007 | Right Linear Auxiliary | $\hat{D} = 9.63$ | 0.0033 |
| | Outer ring D | 0.007 | Right Linear Auxiliary | $\hat{D} = 9.63$ | 0.0033 |
| | Outer ring E | 0.02 | Right Linear Auxiliary | $\hat{D} = 9.5$ | 0.0033 |
| | Outer ring F | 0.01 | Right Linear Auxiliary | $\hat{D} = 9.55$ | 0.0033 |
| | BOT | 1 | iBOT | $\hat{t} = 20$ | 0.98 |
| | All times | 1 | Bound | $D \geq 0$ | — |
| PROMOTING PLAN QUALITY | Target A | 0.12 | Left Linear Auxiliary | $\hat{D} = 16.5$ | 0.055 |
| | Target B | 0.10 | Left Linear Auxiliary | $\hat{D} = 21.5$ | 0.055 |
| | Target C | 0.78 | Left Linear Auxiliary | $\hat{D} = 21.5$ | 0.055 |
| | Target D | 0.99 | Left Linear Auxiliary | $\hat{D} = 21.5$ | 0.055 |
| | Target E | 1 | Left Linear Auxiliary | $\hat{D} = 21.5$ | 0.055 |
| | Target F | 1 | Left Linear Auxiliary | $\hat{D} = 21.5$ | 0.055 |
| | Outer ring A | 0.01 | Right Linear Auxiliary | $\hat{D} = 7$ | 0.0027 |
| | Outer ring B | 0.01 | Right Linear Auxiliary | $\hat{D} = 9.5$ | 0.0027 |
| | Outer ring C | 0.03 | Right Linear Auxiliary | $\hat{D} = 9.5$ | 0.0027 |
| | Outer ring D | 0.04 | Right Linear Auxiliary | $\hat{D} = 9.5$ | 0.0016 |
| | Outer ring E | 0.11 | Right Linear Auxiliary | $\hat{D} = 9.5$ | 0 |
| | Outer ring F | 0.05 | Right Linear Auxiliary | $\hat{D} = 9.5$ | 0.0016 |
| | BOT | 1 | iBOT | $\hat{t} = 20$ | 0.66 |
| | All times | 1 | Bound | $D \geq 0$ | — |

Although an exemplary embodiment of the present invention has been shown and described, it will be apparent to those having ordinary skill in the art that a number of changes, modifications, or alterations to the inventions as described herein may be made. Thus, it is to be understood that the above description of the invention and the accompanying drawings is to be regarded as a non-limiting.

The invention claimed is:

1. A method for treatment planning for a radiation therapy system, the radiation therapy system comprising a radiation therapy unit, wherein a spatial dose delivered can be changed by adjusting beam shape settings, said method being implemented in a treatment planning computer structure including i) a calculation module configured to generate radiation dose profiles to be delivered to a target volume to be treated during a treatment of the patient, to provide a convex optimization problem that steers the delivered radiation according to the objectives, and to calculate dose profiles for specific treatment configurations including beam shape settings for the radiation dose profiles that are calculated using convex optimization problem; ii) a modelling module configured to model a volume of a patient as a three-dimensional voxel representation or to obtain such a three-dimensional voxel representation; iii) a treatment plan module; and iv) an optimizing module, said method comprising the steps of:
setting a number of objectives reflecting clinical criteria for regions of interest, wherein different objectives are set for different regions, including targets to be treated during treatment of the patient, organs at risk and/or healthy tissue and generating radiation dose profiles to be delivered to the target;
modelling radiation dose profiles to be delivered to said target;
providing a convex optimization problem that steers the delivered radiation according to the objectives;
calculating dose profiles for specific treatment configurations including beam shape settings for the radiation dose profiles using said convex optimization problem by means of said calculation module;
creating treatment plans including determining the radiation dose profiles to be delivered during treatment based on the treatment configurations, wherein each radiation dose profile is modelled by a spatial dose volume distribution of radiation, the shape of said spatial distribution depending on the beam shape settings by means of said treatment plan module;
selecting an optimal treatment plan that satisfies the clinical criteria by means of said optimizing module; and
generating an optimized dose plan based on the selected optimal treatment plan and transferring the optimized dose plan to the radiation therapy system for use in the treatment of a patient.

2. The method according to claim 1, wherein the method is for treatment planning for a radiation therapy system, the radiation therapy system comprising a radiation therapy unit having a fixed radiation focus point, wherein a spatial dose distribution surrounding the focus point can be changed by adjusting beam shape setting, including collimator settings, said collimator being arranged in sectors and having a plurality of collimator passage inlets directing radiation emanating from radioactive sources of a source carrier arrangement of the therapy system to said focus point, said method further comprising the steps of:
generating isocenter positions in said target volume;
setting a number of objectives reflecting clinical criteria for the regions of interest, including targets to be treated during treatment of the patient, organs at risk and/or healthy tissue;
providing a convex optimization problem that steers the delivered radiation according to the objectives;
calculating dose rates for specific treatment configurations including sector and collimator settings and irradiation time for the isocenters using said convex optimization problem;

creating treatment plans including determining shots to be delivered during treatment based on the treatment configurations, wherein each shot is modelled by a spatial dose volume distribution of radiation, the shape of said spatial distribution depending on the specific sector and collimator setting and irradiation time; and selecting an optimal treatment plan that satisfies the clinical criteria.

3. The method according to claim 1, further comprising:
defining a set of beam directions;
modelling radiation dose profiles to be delivered to said target as a plurality of beamlets each having a beamlet intensity;
setting a number of objectives reflecting clinical criteria for the target;
providing a convex optimization problem that steers the delivered radiation according to the objectives so as to create fluence maps, wherein the fluence maps define the beamlet intensities for each of said beamlets;
creating treatment plans based on fluence maps and clinical criteria for the target; and
selecting an optimal treatment plan that satisfies the clinical criteria.

4. The method according to claim 1, comprising positioning of radiation source(s) relative to said patient.

5. The method according to claim 2, comprising positioning of radiation source(s) relative to said patient.

6. The method according to claim 4, wherein the step of positioning radiation source(s) includes generating fixed isocenter positions.

7. The method according to claim 5, wherein the radiation source positions are generated as a set of continuous points in said target volume based on basis functions, wherein the points are fixed during the treatment planning.

8. The method according to claim 6, wherein the radiation source positions are generated as a set of continuous points in said target volume based on basis functions, wherein the points are fixed during the treatment planning.

9. The method according to claim 4, comprising selecting zero or one dimensional discrete elements from a basis representation including the target volume.

10. The method according to claim 5, comprising selecting zero or one dimensional discrete elements from a basis representation including the target volume.

11. The method according to claim 4, wherein the step of positioning radiation sources comprises:
performing a reduction process to reduce the number of radiation source positions by solving an initial instance of the convex optimization problem and subsequently excluding positions that did not yield substantial improvements to the clinical criteria in said initial instance of the problem.

12. The method according to claim 5, wherein the step of positioning radiation sources comprises:
performing a reduction process to reduce the number of radiation source positions by solving an initial instance of the convex optimization problem and subsequently excluding positions that did not yield substantial improvements to the clinical criteria in said initial instance of the problem.

13. The method according to claim 1, wherein an objective function of the convex optimization problem is a weighted sum, where each objective is associated with a function and a scalar weight.

14. The method according to claim 2, wherein an objective function of the convex optimization problem is a weighted sum, where each objective is associated with a function and a scalar weight.

15. The method according to claim 14, wherein said objectives include delivered dose to target, delivered dose to a boundary space surrounding said target, delivered dose to regions classified as a risk organ, and/or beam-on time penalization.

16. The method according to claim 1, wherein the step of calculating comprises:
calculating dose rates for specific treatment configurations including sector and collimator settings and irradiation time using said convex optimization problem for predetermined isocenters within said volume.

17. The method according to claim 1, wherein a dose rate is calculated according to a dose rate kernel matrix, $\Phi$, based on sources in a certain collimator state and sector in a certain isocenter location for a certain irradiation time.

18. The method according to claim 1, wherein the dose is given by a function $D(x)$ that depends linearly on x, wherein x corresponds to degrees of freedom.

19. The method according to claim 18, wherein $D(x) = \Phi * x$, and $\Phi$ is a beamlet intensity or a dose rate kernel.

20. The method according to claim 1, wherein the step of calculating comprises:
performing a reduction process to reduce the number of calculated dose rates, wherein a subset of dose rates that are spatially representative are selected for calculation based on an approximation of a volume representation of a delivered dose rate to the target.

21. The method according to claim 1, wherein the step of calculating comprises a reduction process based on truncating estimated dose rates at a predetermined level or applying a statistical model to remove estimated dose rates from the calculation.

22. A treatment planning computer structure integrated into a radiation therapy system having a collimator body provided with several groups or sets of collimator passages, each set being designed to provide a radiation beam of a respective specified cross-section toward a fixed focus, said treatment planning computer structure comprising
a calculation module configured for generating radiation dose profiles to be delivered to a target, for providing a convex optimization problem that steers the delivered radiation according to clinical criteria objectives for optimizing the delivered radiation based on the clinical criteria objectives, wherein different objectives are set for different regions, and for calculating dose profiles for specific treatment configurations including beam shape settings for the radiation dose profiles calculated using a convex optimization function;
a treatment plan module configured for creating treatment plans including determining the radiation dose profiles to be delivered during treatment based on treatment configurations, wherein each radiation dose profile is modelled by a spatial dose volume distribution of radiation, the shape of the spatial distribution depending on the beam shape settings; and
an optimizing module configured for selecting an optimal treatment plan that satisfies the clinical criteria,
wherein a radiation dose plan is generated for delivery to the target through the collimator body according to the selected optimal treatment plan.

23. A method for treatment planning for a radiation therapy system, wherein the method is for treatment planning for a radiation therapy system, the radiation therapy system comprising a radiation therapy unit having a fixed radiation focus point, wherein a spatial dose distribution surrounding the focus point can be changed by adjusting beam shape setting, including collimator settings for a collimator, said collimator being arranged in sectors and having a plurality of collimator passage inlets directing radiation emanating from radioactive sources of a source carrier arrangement of the therapy system to said focus point, said method further comprising the steps of:
  generating non-uniformly spaced isocenter positions in said target volume;
  choosing isocenter positions of the generated fixed isocenter positions for subsequent optimization, wherein each chosen isocenter position represent a subset of the generated isocenter positions;
  setting a number of objectives reflecting clinical criteria for the regions of interest, wherein different objectives are set for different regions including targets to be treated during treatment of the patient, organs at risk and/or healthy tissue;
  providing a convex optimization problem that steers the delivered radiation according to the objectives;
  calculating dose rates for specific treatment configurations including sector and collimator settings and irradiation time for the chosen isocenters using said convex optimization problem;
  creating treatment plans including determining shots to be delivered during treatment based on the treatment configurations, wherein each shot is modelled by a spatial dose volume distribution of radiation, the shape of said spatial distribution depending on the specific sector and collimator setting and irradiation time;
  selecting an optimal treatment plan that satisfies the clinical criteria;
  generating an optimized dose plan based on the selected optimal treatment plan and transferring the optimized dose plan to the radiation therapy system for use in the treatment of a patient.

\* \* \* \* \*